US009562846B2

(12) United States Patent
Kole et al.

(10) Patent No.: US 9,562,846 B2
(45) Date of Patent: Feb. 7, 2017

(54) PARTICLE SUSPENSIONS USED AS LOW-CONTRAST STANDARDS FOR INSPECTION OF LIQUIDS

(71) Applicant: KLA-Tencor Corporation, Milpitas, CA (US)

(72) Inventors: Francisco Kole, San Jose, CA (US); Johannes G. M. Christiaanse, San Jose, CA (US); Greg Kirk, Pleasanton, CA (US); Winfred Tee Chow, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/324,872

(22) Filed: Jul. 7, 2014

(65) Prior Publication Data

US 2015/0015872 A1    Jan. 15, 2015

Related U.S. Application Data

(60) Provisional application No. 61/844,662, filed on Jul. 10, 2013.

(51) Int. Cl.
*G01N 15/02* (2006.01)
*G01N 21/27* (2006.01)
(Continued)

(52) U.S. Cl.
CPC ......... *G01N 21/278* (2013.01); *G01N 15/0227* (2013.01); *G01N 15/06* (2013.01);
(Continued)

(58) Field of Classification Search
CPC  G01N 15/0227; G01N 15/06; G01N 15/0656;
G01N 2001/2893; G01N 2015/0065; G01N 2015/0294; G01N 2015/0687; G01N 2015/0693; G01N 21/278
(Continued)

(56) References Cited

U.S. PATENT DOCUMENTS 5,747,667 A   5/1998   Sadar
6,174,728 B1  1/2001   Ben-David et al.
(Continued)

OTHER PUBLICATIONS

Di Carlo, D. "Inertial microfluidics" The Royal Society of Chemistry, Lab Chip, 2009, 9, 3038-3046, First published as an Advance Article on the web Sep. 22, 2009.
(Continued)

*Primary Examiner* — Tri T Ton
(74) *Attorney, Agent, or Firm* — Meyertons, Hood, Kivlin, Kowert & Goetzel, P.C.; Eric B. Meyertons

(57) ABSTRACT

In certain embodiments, a method for validating the human visual inspection process or an optical analysis instrument for use with biological particles may include inspecting a standard particle solution using the optical analysis instrument. The standard particle solution may include a known concentration of standard particles suspended in solution with the standard particles having a defined size and shape distribution. The standard particles may have a refractive index that is substantially similar to a refractive index of the biological particles. The method may include assessing a concentration of standard particles in the standard particle solution from the inspection. The method may include assessing a difference between the assessed concentration of standard particles and the known concentration of standard particles. The method may include modifying one or more parameters of the optical analysis instrument based on the assessed difference between the concentrations. The method
(Continued)

may include assessing a detection efficiency of the optical analysis instrument.

20 Claims, 2 Drawing Sheets

(51) Int. Cl.
G01N 15/00 (2006.01)
G01N 15/06 (2006.01)
G01N 1/28 (2006.01)

(52) U.S. Cl.
CPC . G01N 15/0656 (2013.01); G01N 2001/2893 (2013.01); G01N 2015/0065 (2013.01); G01N 2015/0294 (2013.01); G01N 2015/0687 (2013.01); G01N 2015/0693 (2013.01)

(58) Field of Classification Search
USPC .................................................. 356/335–343
See application file for complete search history.

(56) References Cited

U.S. PATENT DOCUMENTS 8,162,149 B1* 4/2012 Perroud ............. G01N 15/1484
209/155
2004/0201845 A1* 10/2004 Quist et al. .................... 356/338
2006/0055934 A1* 3/2006 Sunshine et al. ............. 356/446
2009/0128810 A1 5/2009 Bates
2011/0061786 A1* 3/2011 Mason .................. G03F 7/0002
156/62.2

OTHER PUBLICATIONS

Ripple, D. C. et al. "Standards for the Optical Detection of Protein Particles" Amer. Pharm. Rev. 14:90-96, Jul. 1, 2011.

International Search Report and Written Opinion, Application No. PCT/US2014/046096, mailed Jul. 10, 2014, 12 pages.

Knopp et al., "Prediction of the Spatial Resolution of Magnetic Particle Imaging Using the Modulation Transfer Function of the Imaging Process", IEEE Transactions on Medical Imaging, vol. 30, No. 6, Jun. 1, 2011, 9 pages.

Ripple et al., "Standards for the Optical Detection of Protein Particles" Published as Amer. Pharm. Rev. 14:90-96. Jul. 18, 2011.

* cited by examiner

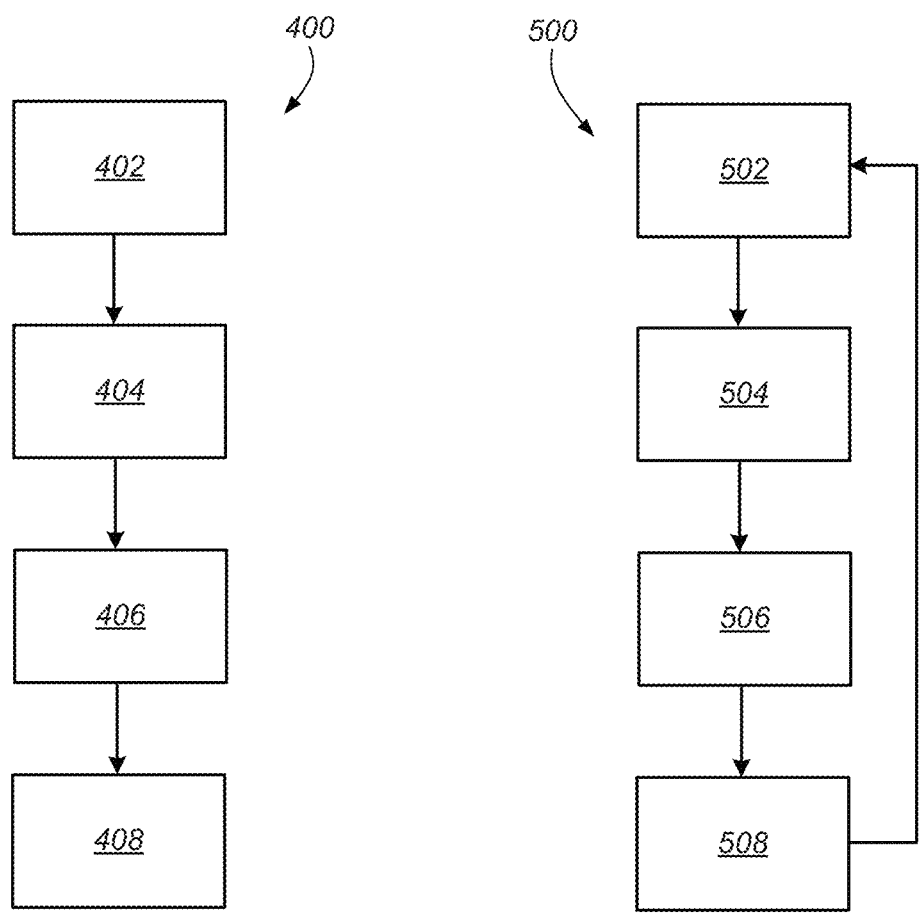

PARTICLE SUSPENSIONS USED AS LOW-CONTRAST STANDARDS FOR INSPECTION OF LIQUIDS

PRIORITY CLAIM

This patent claims priority to U.S. Provisional Patent Application No. 61/844,662 filed Jul. 10, 2013, which is incorporated by reference in its entirety.

BACKGROUND

1. Field of the Invention

The present invention relates to a standard suspension used for inspection of liquids. More particularly, the invention relates to (1) a standard suspension that allows instruments that inspect and classify particle suspensions to be calibrated, validated, and/or compared and (2) a standard for the visual inspection of particle suspensions.

2. Description of Related Art

Biopharmaceutical companies often characterize biological drug products in injectable, liquid form in vials, syringes, or other containers. These containers are typically inspected for the presence of external particles but also can be inspected for particles formed by aggregation of the protein drug substance itself (e.g., in order to determine the safety of a drug product). Additionally, medical device manufacturers that coat medical devices with bio-compatible substances may inspect solutions after washing the devices to look for particles that have sloughed off the devices.

Similarly, in the field of Life Science, optical instruments such as microscopes and flow cytometers are used to analyze particles of biological nature, including biological cells, microvesicles, bacteria and viruses. These particles and protein aggregates, called biological particles henceforth, typically have a low refractive index that is close to that of the solution in which they are presented to the optical instrument.

Visual inspection by the human eye as well as various inspection instruments are used to detect biological particles. Results between human inspectors and instruments may, however, vary and the results may be difficult to compare given the random shapes and sizes of the biological particles and the relatively low contrast the biological particles exhibit because of their small refractive index difference with the solution in which they are suspended. FIG. 1 depicts a photograph of an example of protein aggregation in a container.

In order to assure the efficacy and safety of parenteral drugs, United States Pharmacopeia chapter <788> requires manufacturers of injectable drugs to report a count per unit volume of the number of any particles larger than 10 μm and a count per unit volume of the number of particles larger than 25 μm, including protein aggregate particles. Based on input from the new February 2013 United States FDA (Food & Drug Administration) guidelines that cite increasing concern about immunogenicity caused by protein aggregates, a new chapter with new rules may require monitoring biologic drug products for particulates greater than 2 μm. Protein aggregates may be difficult to detect because their index of refraction (n=~1.34 to 1.40) is close to protein-based drug solutions index of refraction (n=~1.34 to 1.36). There are also a number of different protein agglomerate types that vary in shape and appearance. For example, from ellipsoidal to threadlike (aspect ratios from 0.8 to 0.1) and from amorphous to crystalline.

Current visual inspection relies on the transparency difference between the biologic particles and the surrounding liquid. Instruments used to inspect (detect) micron sized particles typically involve imaging, or light scattering, or light obscuration of the particles as they flow through a clear flow cell. The instruments may use visual and/or machine-based inspection processes. Each of these instruments is calibrated/validated for size measurement accuracy and particle count accuracy by the vendor or a user. Typically, calibration/validation is provided using polystyrene spheres (beads) of a well-defined and uniform diameter and defined concentration. Polystyrene beads are commercially available from vendors such as Thermo Fisher Scientific (Waltham, Mass., U.S.A.), Polysciences, Inc. (Warrington, Pa., U.S.A.), and other vendors.

There are three fundamental drawbacks to optical instrument calibration and validation using polystyrene beads. A first drawback is that polystyrene beads have a higher refractive index (typically n=1.599) than some particles of interest (e.g., protein aggregates with n=~1.34 to 1.40). Thus, the optical signal of polystyrene beads does not adequately represent that of the signal generated by a low-contrast particle of the same size (such as biological particles). Biological particles may generate a lower signal than a polystyrene sphere of the same size due to the refractive index and transparency differences between the particles. As a result, the biological particle may be misclassified and result in erroneous analysis results. In addition, low contrast particle (e.g., biological particle) events may be eliminated from analysis when they generate a signal that falls below the analysis threshold established using polystyrene beads of the same size. This may result in erroneous count results of the low contrast particles. Likewise, the low refractive index makes biological particles more difficult to observe by human eye, also resulting in erroneous count results.

A second drawback is that some biological particles are irregular shaped three-dimensional (3-D) objects rather than uniformly spherical objects (like polystyrene beads). The irregular shapes of biological particles may present certain challenges to the optical analysis instruments. For example, the instrument may only generate a signal based on a two-dimensional (2-D) projection of the 3-D particle. Thus, measuring particles of irregular shape in a flow-through detector may produce wide distributions of instrument response due to random orientation of the particle at the interrogation point. Further, irregular shaped particles may result in a broader size distribution compared to the size distribution of polystyrene beads of the same size. As a result, irregularly shaped particles (such as some biological particles) may be eliminated from the analysis and result in erroneous count results.

A third drawback is that the concentration of polystyrene beads in suspension may vary due to systematic differences in sampling. For example, the parent polystyrene bead suspension may be sampled in the center of the suspension but after beads have begun to settle out of the suspension, resulting in different concentration in later samples.

Thus, it is desired to create a standard suspension that (1) allows the standardization of visual inspection methods and (2) allows optical analysis instruments to be calibrated, validated, and/or compared using standard particles that more closely match the properties of low-contrast and possibly irregular shaped particles such as biological particles. The standard particles in the standard suspension should be stable, reproducible, and have uniformity in key properties to allow operators to properly adjust the instruments or analysis software parameters when necessary. The particle standard suspension should support corrections to defined concentration through the use of an internal concentration standard. Proper adjustment of the instruments and/or the analysis software parameters may allow results to be compared accurately between samples, between analytical instruments, and/or between measurement labs.

SUMMARY

In certain embodiments, a standard particle suspension for use with visual inspection or with an optical analysis instrument may include a solution and a plurality of standard particles. The plurality of standard particles may be suspended in the solution. The plurality of standard particles may have a defined size and shape distribution. The standard particles may have a refractive index that is substantially similar to a refractive index of biological particles.

In certain embodiments, a standard particle suspension provides measurement standards that resemble the properties of biological particles more closely than products currently on the market. These more representative standards will improve instrument calibration, validation, analyses, and comparisons between individual instruments between instrument types and between laboratories.

In certain embodiments, the optical analysis of biological particles with a low refractive index is addressed. Examples of such biological particles may include protein aggregates, biological cells, microvesicles, exosomes, bacteria and viruses.

In certain embodiments, the refractive index of the standard particles is between about 1.34 and about 1.42. The standard particles may have a well-characterized size distribution, for example one that varies within about 10% of a selected standard particle size. The standard particle size may be specifically selected, for example sizes such as: 2 µm, 10 µm, and 25 µm, or any other selected sizes from the range of sizes of biological particles.

In certain embodiments, the standard particles may include polymer material selected from the group consisting of: PTFE, ETFE, PDMS, and FEP.

In certain embodiments, the standard particles and the solution may include one or more additives. The additives may adjust the refractive index difference of the standard particles and the solution to be substantially similar to the refractive index difference of the biological particles in their native solutions.

In certain embodiments, at least one of the standard particles may include one or more patterns. At least one of the patterns may include stripes of varying widths and separations along the length of the standard particle.

In certain embodiments, the suspension may be used for calibration and/or validation of an optical analysis instrument.

In certain embodiments, the suspension may be used for the training and/or certification of visual inspection personnel and for validation of visual inspection protocols.

In certain embodiments, a method for validating an optical analysis instrument for use with biological particles may include inspecting a standard particle suspension using the optical analysis instrument. The standard particles suspended in solution may have a defined size and shape distribution, concentration, and refractive index difference from the solution. The standard particles may have a refractive index that is substantially similar to a refractive index of the biological particles. The method may include assessing a concentration of standard particles in the standard particle solution from the inspection. The method may include assessing a difference between the assessed concentration of standard particles and the known concentration of standard particles. The method may include modifying one or more parameters of the optical analysis instrument based on the assessed difference between the concentrations. The method may include quantifying a correction factor to account for the instrument's detection efficiency. The method may include quantifying a concentration correction factor to account for concentration changes in the standard particle suspension.

In certain embodiments, at least one of the parameters of the optical analysis instrument includes a threshold contrast level. At least one of the parameters of the optical analysis instrument may include an image processing parameter. At least some of the standard particles may include one or more MTF (modulation transfer function) testing patterns. The method may include assessing optical performance of the optical analysis instrument using the MTF testing patterns and modifying one or more parameters based on the assessment.

In certain embodiments, the method may include a size distribution of the standard particles in the standard particle suspension from the inspection.

In certain embodiments, the method may include reporting a measured shape distribution of the standard particles in the standard particle solution.

In certain embodiments, the method may include standard particles with a refractive index similar to biological particles or a refractive index difference between the standard particles and the solution similar to biological particles and their native solution.

In certain embodiments, the method may include standard particle suspension of known concentration.

In certain embodiments, the method may include standard particle suspension with more than one population of standard particles, each with different size distributions, or different shape distributions, or different refractive index, or different concentration.

In certain embodiments, a method for forming a standard particle suspension may include forming a plurality of standard particles from a polymer material. The method may include selecting standard particles of similar size and shape to provide a plurality of standard particles with a similar sizes and shapes. The method may include placing the standard particles in a solution, wherein the standard particles in the solution have a refractive index that is substantially similar to a refractive index of biological particles. The method may include assessing a concentration of the standard particles in the solution.

In certain embodiments, the method may include forming the standard particles using a lithography process.

In certain embodiments, the method may include selecting the standard particles of similar size and shape using a filtering process.

In certain embodiments, the refractive index of the standard particles in solution is between about 1.34 and about 1.42.

In certain embodiments, the method may include reporting a measured size and/or shape distribution, and/or refractive index, and/or concentration of the particles in the solution. Some of these measurements may be traceable to SI units.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 4 depicts a flowchart of an embodiment of a process for making a standard particle solution.

FIG. 5 depicts a flowchart of an embodiment of a process for validating an optical analysis instrument using a standard particle solution.

Figure 1:
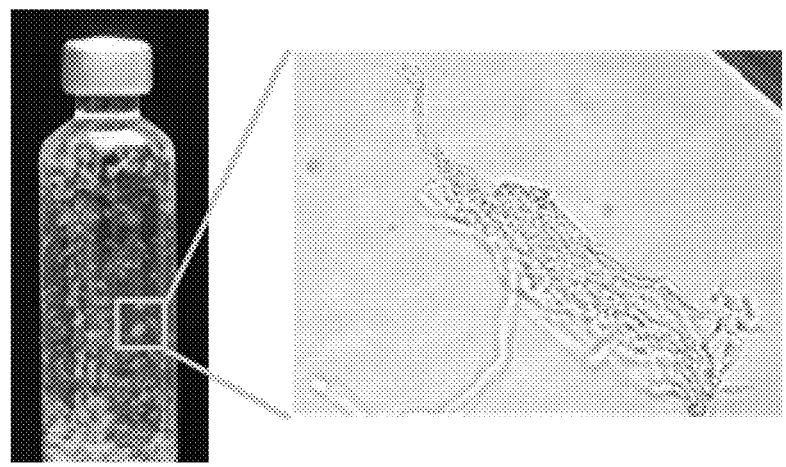
FIG. 1 depicts a photograph of an example of protein aggregation in a container.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

Figure 2:
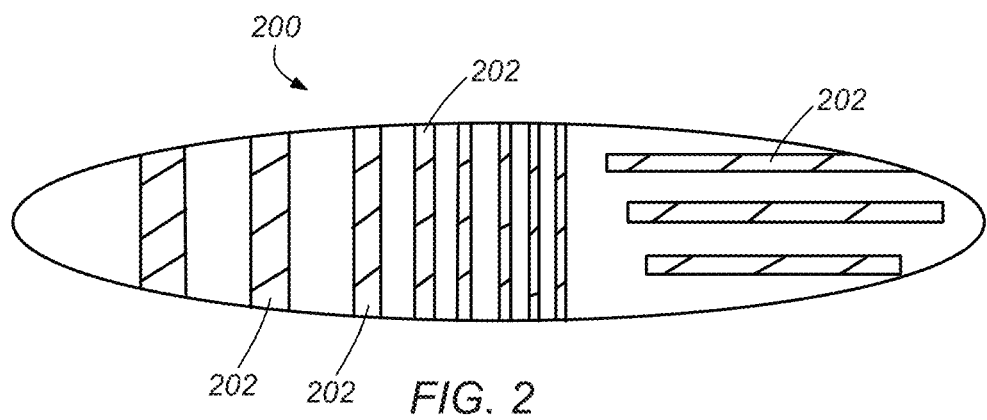
FIG. 2 depicts a representation of an embodiment of a standard particle used in a standard suspension. The standard particle may be uniform or nonuniform in shape and may include one or more materials, and may contain a test pattern.

FIG. 2 depicts a representation of an embodiment of a standard particle used in a standard suspension. Standard particle 200 may be used in a fluid suspension that is used as a standard suspension for optical analysis instruments. The standard suspension may be used for calibration, validation, and/or comparison of optical analysis instruments. Optical analysis instruments include, but are not limited to, instruments that optically inspect fluid suspensions for the presence of particles (e.g., identify the particles) using either visual or machine-based processes. Such optical analysis instruments may also measure or assess one or more characteristics of the identified particles. Characteristics may include, for example, size and/or shape, and/or transparency/opacity, and/or concentration of the particles.

In certain embodiments, standard particle 200 has substantially similar materials properties to a biological particle. For example, standard particle 200 may have a refractive index, a specific gravity, a size, and/or a shape that is substantially similar to a biological particle. In certain embodiments, standard particle 200 is formed from a polymeric material. Examples of polymeric materials for standard particle 200 include, but are not limited to, PTFE (polytetrafluoroethylene) (e.g., Teflon®), ETFE (ethylene tetrafluoroethylene) (e.g., Tezfel® or Fluon®), PDMS (polydimethylsiloxane) (e.g., Sylgar®) or FEP (fluorinated ethylene propylene, which is a copolymer of hexafluoropropylene and tetrafluoroethylene). These materials may have a refractive index substantially similar to biological particles. For example, PTFE may have a refractive index, n, of 1.350, ETFE may have a refractive index of 1.398, and PDMS may have a refractive index of 1.4118.

Figure 3:
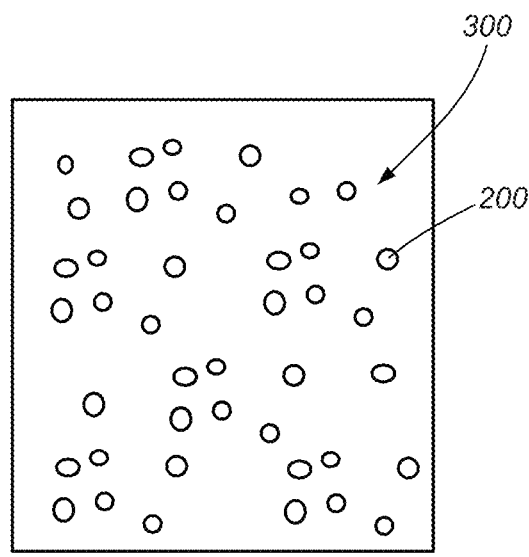
FIG. 3 depicts a representation of an embodiment of standard particles in solution.

FIG. 3 depicts a representation of an embodiment of standard particles 200 in solution 300. Standard particles 200 may be placed in solution 300 to form a standard particle suspension (e.g., a standard suspension). In certain embodiments, solution 300 is a buffer solution. Solution 300 may have properties and/or include additives that adjust the refractive index difference and/or buoyancy of standard particles 200 to more accurately match the refractive index difference and/or buoyancy of selected biological particles in their formulized buffer solutions. For example, sugar, glycerol, or other additives may be provided to solution 300 to adjust the refractive index difference and/or buoyancy of standard particles 200 in the solution. In certain embodiments, standard particles 200 in solution 300 have a refractive index between about 1.34 and about 1.42. In some embodiments, standard particles 200 in solution 300 have a refractive index between about 1.3 and about 1.45, between about 1.32 and about 1.43, or between about 1.34 and about 1.4.

In certain embodiments, standard particles 200 in solution 300 have substantially similar optical properties as biological particles such that the standard particle can be used to calibrate and/or validate an optical analysis instrument for analysis of biological particles in solution. For example, standard particles 200 in solution 300 may be used to calibrate and/or validate the size response of the optical analysis instrument. In certain embodiments, standard particles 200 provide the same optical contrast as biological particles. Standard particles 200 may, unlike the biological particles, however, have substantially uniform size and shape in solution 300. In certain embodiments, standard particles 200 include standard particles with a tight size distribution around selected count threshold sizes. Count threshold sizes may be maximum and/or minimum sizes (e.g., diameters) at which a count for a number of particles is conducted (e.g., a particle count is found for particles below and/or above the count threshold sizes). Typical count threshold sizes for biological particles may be, for example, about 2 μm, about 10 μm, or about 25 μm. Thus, in some embodiments, standard particles 200 have tight size distributions around about 2 μm, around about 10 μm, or around about 25 μm. The tight size distribution may be, for example, within about 1%, within about 5%, or within about 10% of the selected size.

FIG. 4 depicts a flowchart of an embodiment of process 400 for making a standard particle solution. In 402, standard particles (e.g., standard particles 200) are formed from a polymer material using one or more processes described herein. In 404, standard particles of selected sizes and shapes (e.g., similar sizes and shapes) are selected to provide a plurality of standard particles with similar sizes and shapes. For example, the formed standard particles may be filtered or otherwise selected as described herein to provide a plurality of standard particles with similar sizes and shapes. In 406, the standard particles may be placed in a solution (e.g., solution 300). In certain embodiments, the standard particles in solution (e.g., standard particles 200 in solution 300) may have other desired qualities, for example a particular refractive index or specific gravity. In 408, a concentration of the standard particles may be assessed (e.g., measured) using techniques described herein. In some embodiments, a size and/or shape of the standard particles is assessed (e.g., measured) using techniques described herein.

In certain embodiments, forming standard particles in 402 includes making standard particles (e.g., standard particles 200) from commercially available powders (e.g., powders of PTFE, ETFE, PDMS, or FEP). For example, standard particles may be made by filtering the powders to selected powder particles of the desired (selected) size and shape distributions. The powders may be filtered, for example, using dry or wet sieves, Field-Flow Fractionation (FFF), other fluidic selection methods, and/or combinations thereof. As an example, PTFE powder may be obtained from Polysciences, Inc. (Warrington, Pa., U.S.A.) and filtered using a Field-Flow Fractionation system obtained from Postnova Analytics, Inc. (Salt Lake City, Utah, U.S.A.) to produce PTFE standard particles of a selected size and shape distribution.

In certain embodiments, standard particles are made using lithographic and/or etch processes. For example, standard particles may be made using traditional semiconductor lithographic and etch processes. In an embodiment, a silicon wafer (e.g., a 4" silicon wafer) may have a hardened photoresist (e.g., SU-8 photoresist) patterned on the surface of the wafer. The plastic material (e.g., either powder or liquid plastic material) may be filled into the pattern formed by the photoresist to form standard particles of selected shapes and/or sizes. The standard particles may be released from the surface using, for example, vibration, air flow, or submerging in an ultrasonic bath.

In some embodiments, particles are made with newer embossing or stamping lithographic processes using a die such as nanoimprint lithography (NIL) or lithography-electroplating-molding processes (such as LIGA, UV-LIGA, or Force-LIGA). Embossing or stamping lithographic processes may be useful in producing standard particles for materials such as FEP. Some of the newer embossing or stamping lithographic processes are capable of producing features on a die down to about 50 nm in size with large aspect ratios in various plastic materials from various lithographically-generated die.

A die may be made of, for example, silicon, silicon carbide, quartz, or metal. The die may be a mold or roller may have shapes formed in or protruding from the surface of the mold or roller. The die may then be pressed into a plastic film or filled with plastic material (e.g., plastic powder or liquid) to form standard particles with desired shapes and sizes in the plastic material. For example, under pressure, the die (mold) may be pressed into plastics that are pre-softened by heating, pressed into plastics that are in a pre-cured liquid state, or embossed into a plastic film Producing such features on a die may provide mass production of desired (selected) standard particle shapes with desired (selected) sizes (e.g., produce standard particles 200 with desired shape and size distributions for use in standard suspensions).

In one embodiment, a thin mold in the 1-100 μm regime may be made with mold shapes that are irregular and appear like aggregates (e.g., protein aggregates). Plastics such as PDMS may be molded into the thin mold. In another embodiment, embossing or nanoimprint lithography (NIL) techniques may be applied to films or layers of plastic materials (e.g., ETFE, PTFE, PDMS). These embossed or imprinted films may be used to construct desired standard particles. In yet another embodiment, a combination of different forms of plastic materials (e.g., film, particle, or liquid) may be used to fabricate standard particles with specially-tuned characteristics such as, but not limited to, refractive index or buoyancy.

In certain embodiments, the lithographic or etch techniques and, possibly, additional treatments may be used to provide precise modifications of standard particle appearance and/or other characteristics. Thus, these techniques may provide mass production of controlled biological particle standards variants that may be engineered to reproduce the appearance of specific types of biological particles. For example, in some embodiments, the die used in an embossing or stamping may be engineered to produce surface features on the standard particles that make them appear more amorphous (fuzzy) or more crystalline (hard-edged).

Other surface modifications to the die (and/or to the standard particles) include plasma or chemical (solvent) etch treatments that may fog or crack the surface. Such modifications may provide controlled modification of the standard particle appearance. Plasma or chemical etch treatments may also provide a method to reduce the hydrophobicity of the plastic materials. Reducing the hydrophobicity of the plastic materials used for the standard particles may further mimic the behavior of biological particles.

In some embodiments, the lithographic processes described allow for the inclusion of other materials into or alongside the primary plastic material. The other materials may be layered in different layers in the standard particle (e.g., the standard particle has multiple layers with different materials in one or more of the layers). These included materials may alter the optical appearance and/or the buoyancy of the standard particles in a liquid (e.g., standard particles 200 in solution 300). These modifications may involve the inclusion of trapped bubbles of air or another specific gas and/or involve mixing or copolymerization using other materials that differ in the refractive index or in the specific gravity from the primary material.

In certain embodiments, the standard particles formed and entrapped in the mold of the plastic materials are freed (e.g., divided into the standard particles) using an etch process. For example, reactive ion etching (RIE) is useful for etching fluoropolymers to free (divide or separate) the plastic material mold into the desired standard particles. Producing standard particles 200 using the lithographic and/or etch processes described may provide production of desired standard particles with high throughput (e.g., mass production). The standard particles produced may be produced with precise and defined production protocols that may be standardized across multiple production sites.

In some embodiments, standard particles are made by abrading particles from solid material. An example of forming standard particles from abrasion is found in "Standards for the Optical Detection of Protein Particles"; Dean C. Ripple, Joshua R. Wayment, Michael J. Carrier; Biochemical Science Division, NIST, Gaithersburg, Md.; published as *Amer. Pharm. Rev.* 14:90-96, Jul. 10, 2011, which is incorporated by reference as if fully set forth herein.

In certain embodiments, selecting standard particles in 404 includes selectively isolating standard particles of similar size and shape. For example, filtration, dry or wet sieves, Field-Flow Fractionation, and/or other fluidic selection methods may be used to select standard particles of similar size and shape for use in a standard suspension. Some additional examples of size selection include, but are not limited to, filtering the suspension using a sequence of mesh sizes or electroformed grid sieves, sedimentation Field-Flow Fractionation, centrifugation followed by aspiration of the small standard particles, continuous internal focusing in flow (see, e.g., Dino DiCarlo, "Inertial Microfluidics", *Lab On A Chip*, Royal Society of Chemistry, 2009, 9, 3038-3046, which is incorporated by reference as if fully set forth herein), and/or cross flow fractionation.

In certain embodiments, assessing of standard particles in 408 includes measuring size and/or concentration of the standard particles in solution. Measurement of size may use any number of techniques in combination with appropriate measurement standards that may establish traceability back to SI units (typically a standard reference material from a national standards lab such as NIST). These techniques may include one or more of the following techniques: optical microscopy, TEM (transmission electron microscope) or wet E-TEM microscopy, SEM (scanning electron microscope) microscopy, Coulter counter, nanopore measurement (systems made by Izon Science Ltd, Oxford, UK), microfluid imaging (e.g., systems made by Fluid Imaging Technologies (Scarborough, Me., U.S.A.) or Protein Simple (Santa Clara, Calif., U.S.A.), dynamic light scattering, or light obscuration methods. Measurements of concentration may include use of one or more of the following techniques: Coulter counter, nanopore measurement, optical microscope, microfluid imaging, dynamic light scattering, or light obscuration methods. In some embodiments, shape of the particles is also measured.

Measurements of size and/or concentration may be made at the batch level or at the individual unit level for the standard particles. Batch level measurements may be statistically-valid measurements of size, shape, and concentration that are representative of a large quantity of standard particles from a single production run or from a stable manufacturing process. Units distributed out (shipped) may be extracted from the large batch quantity. Unit level measurements may be made for each shipped unit, with the sizes, shapes, and counts representing only the contents of the single unit.

In certain embodiments, the count performance of an optical analysis instrument is validated and/or calibrated using a standard particle suspension of known concentration in which the standard particles resemble the low contrast particles of interest (e.g., biological particles). For example, the standard particle suspension may include standard particles 200 formed as described herein and placed in solution 300, as shown in FIG. 3. FIG. 5 depicts a flowchart of an embodiment of process 500 for validating an optical analysis instrument using the standard particle suspension.

In 502, the standard particle suspension may be inspected using the optical analysis instrument. The standard particle suspension may have a known concentration of standard particles suspended in the solution (e.g., as assessed in 408 above). In 504, the concentration of standard particles in the solution may be assessed as measured by the optical analysis instrument (e.g., from the optical inspection). In 506, a difference between the assessed concentration and the known concentration may be assessed (e.g., evaluated). In 508, one or more parameters of the optical analysis instrument may be modified based on the assessed difference between the concentrations. After modification of the parameters, process 500 may be repeated using the new parameters. Process 500 may be repeated until assessed concentration found using the optical analysis instrument matches the known concentration of standard particles in the standard particle suspension. Process 500 may result in an assessment of the optical analysis instrument's detection efficiency if the assessed concentration does not match the known concentration of the standard particles in the standard particle suspension.

In certain embodiments, the resemblance between standard particles 200 in solution 300 and the biological particles of interest includes resemblance in transparency and refractive index as well as size and shape. In an embodiment of 508, a user of the optical analysis instrument may modify the instrument recipe parameters (e.g., threshold contrast levels, image processing parameters, etc.) until the expected counts are achieved using the standard particle suspension (e.g., standard particles 200 in solution 300) or until a detection efficiency for the instrument can be quantified. Subsequently, the user may have more confidence in the actual counts of biological particles in certain size ranges using the optical analysis instrument because the optical analysis instrument has been calibrated and/or validated with particles (e.g., standard particles 200) that have similar properties to the biological particles.

In certain embodiments, the standard particle suspension (e.g., standard particles 200 in solution 300) provides the user of the optical analysis instrument with a characterized standard that is documented in one or more physical parameters. These parameters may be related to distributions of standard particle size, shape, refractive index, and concentration and may apply to one or more metrics for each type of measurement performed by the optical analysis instrument. Examples of these metrics include, but are not limited to, Feret diameter and equivalent circle diameter (ECD) for size, and aspect ratio (AR) and circularity for shape. Documenting the standards may serve as rigorous baseline that can be used to quantify the sensitivity of the optical analysis instrument. The optical analysis instrument's sensitivity may be evaluated based on its detection rate for standard particles of specific sizes, shapes, or other documented physical characteristic and the concentration of that component in the standard.

In certain embodiments, a combination of standard particle suspensions provides an internal standard for assessing concentration changes A standard particle suspension may include more than one population of standard particles, each with a defined concentration, that are alike in every defined parameter, except in refractive index. At least one opaque population may be provided that has a high detection rate in the optical analysis instrument. The method may include assessing change in the concentration of the one or more opaque populations and applying such a measured change to modify the starting concentrations for the one or more nearly-transparent standard particle populations.

In some embodiments, the standard particle suspension (e.g., standard particles 200 in solution 300) allows results from different instruments or different measurement laboratories and/or results found from different analytical methods to be compared. Since the standard particle suspension has been characterized and has a determined size and shape distribution, and a refractive index, the standard particle suspension allows the comparison of these other (possible) variables. In some embodiments, the standard particle suspension allows proper documentation of consistent instrument performance over time.

In some embodiments, standard particles 200 include one or more patterns 202, as shown in FIG. 2. Patterns 202 may be designed to generate a wide range of spatial frequencies. In addition, images of patterns 202 may be used to measure the MTF (modulation transfer function) of the optical analysis instrument. Measuring the MTF of the optical analysis instrument may be used to calibrate the instrument and/or match the instrument with other instruments. In some embodiments, standard particles 200 are immersed in solution 300 and the solution has properties and/or includes additives that adjust the refractive index difference of the standard particles and/or patterns 202 on the standard particles with the solution 300.

In certain embodiments, as shown in FIG. 2, standard particle 200 is a smooth rod-shaped standard particle with patterns 202. Patterns 202 may include stripes of varying widths and separations along the length of standard particle 200. In some embodiments, patterns 202 include an MTF testing pattern. The MTF testing pattern may be used to measure microscope optical performance using standard particle 200. Standard particle 200 may, however, include other patterns 202 and/or have other shapes that may be used to assess sensitivity of a microscope system (e.g., the optical analysis instrument). In some embodiments, patterns 202 may be layered in standard particle 200. Layered patterns 202 may be used to test resolution and/or focus at different distances from the camera or scope of the optical analysis instrument.

In some embodiments, a longer dimension of standard particle 200 travels parallel to the fluid flow in the optical analysis instrument (shown by the arrow in FIG. 2). In some embodiments, standard particle 200 is designed to cover a field of view of the optical analysis instrument. For example, standard particle 200 may fit within a flow cell of the optical analysis instrument. Standard particle 200 may include rounded and/or smooth edges, and/or a hydrophilic surface to inhibit the standard particle from binding or clogging in the flow cell.

It is to be understood the invention is not limited to particular systems described which may, of course, vary. It is also to be understood that the terminology used herein is for the purpose of describing particular embodiments only, and is not intended to be limiting. As used in this specification, the singular forms "a", "an" and "the" include plural referents unless the content clearly indicates otherwise. Thus, for example, reference to "a shape" includes a combination of two or more shapes and reference to "a liquid" includes mixtures of liquids.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A standard particle suspension configured for use with at least one of human visual inspection and an optical analysis instrument, comprising:
    a solution;
    one or more pluralities of standard particles suspended in the solution, wherein each plurality of standard particles has a defined size and shape distribution, and wherein the standard particles have a defined refractive index and a buoyancy that is similar to biological particles; and
    one or more additives in the solution, wherein the additives adjust the refractive index difference of the standard particles with the solution to be similar to the refractive index difference of the biological particles and their native solution.

2. The suspension of claim 1, wherein the selected standard particle size ranges from about 1 nanometer to about 1 millimeter.

3. The suspension of claim 1, wherein the standard particles comprise polymer material selected from the group consisting of: PTFE, ETFE, PDMS, and FEP.

4. The suspension of claim 1, wherein at least one of the standard particles comprise one or more patterns.

5. The suspension of claim 4, wherein at least one of the patterns include stripes of varying widths and separations along the length of the standard particle.

6. The suspension of claim 1, wherein the suspension is used for at least one of calibration and validation of an optical analysis instrument.

7. A standard particle suspension configured for use with at least one of human visual inspection and an optical analysis instrument, comprising:
    a solution;
    one or more pluralities of standard particles suspended in the solution, wherein each plurality of standard particles has a defined size and shape distribution, wherein the standard particles have a defined size distribution around a selected particle size, and wherein the standard particles have a defined refractive index and a buoyancy that is similar to biological particles; and
    one or more additives in the solution, wherein the additives adjust the refractive index difference of the standard particles with the solution to be similar to the refractive index difference of the biological particles and their native solution.

8. The suspension of claim 7, wherein the refractive index of the standard particles ranges from values that render the standard particle transparent in solution to opaque in solution.

9. The suspension of claim 7, wherein the selected standard particle size ranges from about 1 nanometer to about 1 millimeter.

10. The suspension of claim 7, wherein the standard particles comprise polymer material selected from the group consisting of: PTFE, ETFE, PDMS, and FEP.

11. The suspension of claim 7, wherein at least one of the standard particles comprise one or more patterns.

12. The suspension of claim 11, wherein at least one of the patterns include stripes of varying widths and separations along the length of the standard particle.

13. The suspension of claim 7, wherein the suspension is used for at least one of calibration and validation of an optical analysis instrument.

14. A standard particle suspension configured for use with at least one of human visual inspection and an optical analysis instrument, comprising:
    a solution;
    one or more pluralities of standard particles suspended in the solution, wherein each plurality of standard particles has a defined size and shape distribution, wherein the standard particles have a defined refractive index and a buoyancy that is similar to biological particles, and wherein the refractive index of the standard particles ranges from values that render the standard particle transparent in solution to opaque in solution; and
    one or more additives in the solution, wherein the additives adjust the refractive index difference of the standard particles with the solution to be similar to the refractive index difference of the biological particles and their native solution.

15. The suspension of claim 14, wherein the standard particles have a defined size distribution around a selected particle size.

16. The suspension of claim 14, wherein the selected standard particle size ranges from about 1 nanometer to about 1 millimeter.

17. The suspension of claim 14, wherein the standard particles comprise polymer material selected from the group consisting of: PTFE, ETFE, PDMS, and FEP.

18. The suspension of claim 14, wherein at least one of the standard particles comprise one or more patterns.

19. The suspension of claim 18, wherein at least one of the patterns include stripes of varying widths and separations along the length of the standard particle.

20. The suspension of claim 14, wherein the suspension is used for at least one of calibration and validation of an optical analysis instrument.

* * * * *